United States Patent [19]

Bradley et al.

[11] 4,184,038

[45] Jan. 15, 1980

[54] SYNTHESIS OF ERYTHROMYCIN ETHYL CARBONATE

[75] Inventors: Arthur Bradley, Sandbach; Roger J. Coles, Gosport, both of England

[73] Assignee: American Cyanamid Company, Stamford, Conn.

[21] Appl. No.: 866,894

[22] Filed: Jan. 3, 1978

[30] Foreign Application Priority Data

Jan. 4, 1977 [GB] United Kingdom ............... 0081/77

[51] Int. Cl.$^2$ ............................................. C07H 17/08
[52] U.S. Cl. ............................................. 536/9; 424/180
[58] Field of Search ................ 536/9; 260/343; 539/9

[56] References Cited

U.S. PATENT DOCUMENTS

| 3,040,025 | 6/1962 | Murphy et al. | 536/9 |
| 3,417,077 | 12/1968 | Murphy et al. | 536/9 |

*Primary Examiner*—Johnnie R. Brown
*Assistant Examiner*—Blondel Hazel
*Attorney, Agent, or Firm*—Claude J. Caroli

[57] ABSTRACT

This invention relates to a process for preparing erythromycin ethyl carbonate and to erythromycin ethyl carbonate produced thereby.

7 Claims, No Drawings

SYNTHESIS OF ERYTHROMYCIN ETHYL CARBONATE

SUMMARY OF THE INVENTION

A known process for the synthesis of erythromycin ethyl carbonate involves the use of acetone as solvent. For instance U.S. Pat. No. 3,040,025 which describes the preparation of various erythromycin esters teaches the addition of ethyl chlorocarbonate to a solution of erythromycin and sodium carbonate in acetone to obtain erythromycin ethyl carbonate (referred to hereinafter as E.E.C.).

Although E.E.C. of a fairly reasonable quality can be made by this process the overall yield is low and E.E.C. formation is accompanied by the formation of substantial quantities of O,N-Dicarbethoxy (O.N.D.C.) impurity.

The formation of both E.E.C. and O.N.D.C. is via a polar quaternary nitrogen intermediate. We have carried out an investigation to examine the effect of solvent polarity on the yield and quality of the product using commercially available solvents whose polarities cover a wide range according to the Hildebrand scale of solvent polarities.

As a result of these examinations we have observed that alkanols and alkoxy alkanols can be used to provide satisfactory alternative solvent systems for the reaction.

DETAILED DESCRIPTION OF THE INVENTION

According to a broad aspect of the invention we provide a process for preparing erythromycin ethyl carbonate, comprising reacting ethyl chloroformate with erythromycin in an alkanol or an alkoxyalkanol solvent containing a weak base, and thereafter separating erythromycin ethyl carbonate from the reaction mixture.

Preferred alkanols are $C_2$-$C_5$ alkanols, most preferably isopropanol.

The most preferred solvent is 2-methoxyethanol.

The preferred weak bases are sodium bicarbonate and sodium carbonate: among the weak bases we have found can be used are, e.g., sodium bicarbonate, triethylamine, ammonia, ethanolamine, isopropylamine, diosopropylamine, and sodium carbonate.

The reaction is generally carried out at 35° to 65° C. e.g. 50°-55° C.; reaction periods may be e.g. from 3 to 5 hours.

In embodiments described hereunder, after reaction any insoluble salt is removed, the filtrate drowned with at least an equal volume of water, and the aqueous mixture aged to precipitate the erythromycin ethyl carbonate.

A general form of our process is to add ethyl chloroformate (in solution in the chosen solvent) at a given temperature, over a predetermined time to a solution of erythromycin in the solvent containing preferably sodium bicarbonate. The bicarbonate scavenges hydrogen chloride formed in the reaction; sodium chloride precipitates, is removed and the filtrate drowned in an excess of water. The resulting precipitate is isolated by filtration.

Results of operations carried out in accordance with the general directions in the above paragraph are given below in Table 1 in which (except where indicated) the solvent used was isopropanol and the excess of water was five fold, and other parameters were identical for each reaction.

TABLE 1

| Run No. | Temp. °C. | Chloroformate Addition Time (Mins) | Stirring Time after addition (Mins) | Crude Yield % * | Soluble O.N.D.C. % ** A | Insoluble O.N.D.C. % ** | Base % ***B |
|---|---|---|---|---|---|---|---|
| 1 | 0 | 30 | 0 | 45 | 1.6 | 0 | 4 |
| 2 | 0 | 30 | 240 | 42 | 1.9 | 0 | 5 |
| 3 | 0 | 30 | 240 | 38 | — | — | - C |
| 4 | 0 | 30 | 0 | 44 | 1.4 | 0 | 4 D |
| 5 | 20 | 30 | 0 | 45 | 9.8 | 0 | 5 |
| 6 | 20 | 210 | 0 | 17 (pure) | — | 11.4 | - G |
| 7 | 40 | 1 | 30 | 56 | 11.2 | 0 | 4 |
| 8 | 40 | 1 | 30 | 75 | 11.0 | 0 | 5 E |
| 9 | 40 | 30 | 0 | 94 | 7.0 | 0 | 6 F |
| 10 | 40 | 30 | 0 | 71 | 9.8 | 0 | 6 |
| 11 | 40 | 30 | 0 | 39 | 11.2 | 0 | 6 D |
| 12 | 40 | 150 | 0 | 75 | 1.9 | 0 | 6 |
| 13 | 40 | 180 | 0 | 88 | 9.4 | 0 | 4 |
| 14 | 40 | 240 | 0 | 85 | 0.9 | 0 | 6 |
| 15 | 40 | 270 | 60 | 48 | 5.8 | 2.0 | 5 |
| 16 | 55 | 90 | 0 | 74 | 4.2 | 0 | 6 |
| 17 | 55 | 210 | 0 | 65 (pure) | 0.96 | 3.0 | <4 G |
| 18 | 70 | 30 | 0 | 74 | 8.5 | 0 | 5 |
| 19 | 85 | 210 | 0 | 69 (pure) | 2.3 | 1.0 | >4 G |
| 20 | 100 | 210 | 0 | 37 (pure) | 1.6 | 6.9 | >4 G |

TABLE 1-continued

| Run No. | Temp. °C. | Chloroformate Addition Time (Mins) | Stirring Time after addition (Mins) | Crude Yield % * | Soluble O.N.D.C. % ** A | Insoluble O.N.D.C. % ** | Base % *** B |
|---|---|---|---|---|---|---|---|
| 21 | 122 | 210 | 0 | zero | — | — | - G |

Notes
A O.N.D.C. is O,N-Dicarbethoxy impurity
B Base content by T.L.C. examination
C Allowed to stand overnight at 0° C.
D Using ½ mole excess of ethyl chloroformate
E Using neat ethyl chloroformate
F Fast stirring rate - all other reactions using fixed slow stirring rate
G Solvent used was 2-methoxyethanol and reaction mixture drowned into three volumes of water
\* yield % is the weight solids product as a percentage of the theoretical E.E.C. product
\*\* % O.N.D.C. is the weight O.N.D.C. as a percentage of the total product
\*\*\* % base is weight of base unreacted as a percentage of the total product The above data in Table 1 illustrates the following points outlined below.

(a) when using isopropanol as solvent insoluble O.N.D.C. formation was found to occur only in reaction 20, where a 4½ hour addition time and a 1 hour post-addition stir out was used. Using 2-methoxyethanol as solvent gave some insoluble O.N.D.C. but tended to reduce the soluble O.N.D.C. levels.

(b) all the reactions carried out at 0° C. including the use of extended reaction times and excess of ethyl chloroformate, gave yields of 40-45% of products all of which were low in O.N.D.C. content. It would appear from these preliminary results that at this temperature an equilibrium reaction is taking place.

(c) increased yields are obtained at temperatures up to 85° C. and the O.N.D.C. content is reduced when the addition time is extended to between 2½ and 4 hours.

(d) apart from the cold reactions, allowing the reaction solution to stand after the chloroformate addition increases the O.N.D.C. content.

(e) the base content of the product is higher than that obtained using acetone as solvent; this is presumably due to the decreased solubility of the base in isopropanol/water compared to acetone/water and the fact that a higher water/solvent ratio is needed using isopropanol. Subsequent recrystallization indicates that the base content can be reduced by recrystallization from acetone/water. The use of 2-methoxyethanol as the solvent gave base levels of approximately 4%.

On laboratory scale experiments, the processes we have carried out in accordance with our invention have given better yields of better quality product, using high temperature/long addition time conditions, than the existing method of manufacture.

The levels of O.N.D.C. (i.e. the O,N-dicarbethoxy derivative) obtained using the older acetone process, were frequently above the acceptable level when the product (Erythromycin Ethyl Carbonate) was controlled by the B.P. specification, especially when the process was carried out on the pilot scale as opposed to the bench scale, whereas with the preferred practice of our processes the O.N.D.C. level can be kept to within the B.P. specification. In fact, in the processes we describe using 2-methoxyethanol there is usually little insoluble O.N.D.C. obtained and only a few percent of the soluble O.N.D.C. by-product. This not only increases the yield, but enables the product to be released within the B.P. specification.

Tables 2 to 4 below summarize some of the data on the synthesis of E.E.C. under the same temperature and time conditions used in obtaining the results of Table 1 obtained using 2-methoxyethanol as solvent. The data includes the preliminary laboratory scale runs together with 3 pilot plant scale runs (Table 2).

Several points can be seen in the data from the three plant runs (Table 2).

1. The yields of crude E.E.C. are higher than those experienced with the isopropanol process—an increase of 5-10%. Allowing for refining, this method is expected to give overall yields for the process somewhere in the range 80-90% (c.f. 70-75% using isopropanol).

2. The O.N.D.C. levels are very low. No "ether insoluble" O.N.D.C. was detected in any of the plant batches, and the highest "ether soluble" O.N.D.C. content found was 2%. This is even allowing for the fact that in this process an excess of ethyl chloroformate is used without apparently causing O.N.D.C. formation. In the other processes (using either acetone or isopropanol) the quantity of ethyl chloroformate required careful monitoring, as any excess resulted in considerable O.N.D.C. formation. This means that use of 2-methoxyethanol is likely to be more resistant to operator error on manufacturing plant as less stringent conditions are required.

3. The rate of addition and the total addition time require less exacting conditions than processes used hitherto. The runs using 2-methoxyethanol were carried out using an addition time of 3¾ hours, as opposed to 5 hours using isopropanol, and it may be possible for this time to be reduced further. Also, from experience in the plant, the rate of addition does not require such critical control using this process.

4. It should also be noted that the product from the 2-methoxyethanol process filters much better than products from processes using e.g. acetone/water and even isopropanol/water. Typically, a 5 kg batch from 2-methoxyethanol/water filters in 2½-3 hours, compared to a 4 kg batch using isopropanol/water which takes approximately 6 hours; also the filter cake from 2-methoxyethanol/water is firmer, drier and requires around 30-40% less drying time in the oven.

5. 2-Methoxyethanol is easier to recover from aqueous solutions for recycling purposes than any previous solvents used, which would be useful if ever large scale manufacture is undertaken.

6. Variations of reaction solvent volume are shown in Table 3. The results indicate that a decrease in volume increased the yield of product, but had an adverse effect on quality.

7. In these runs the effect of drown-out water volume has been examined (Table 4). It can be seen that changes in drown-out volume from 1 vol to 8 vols had little effect on yield or on product quality.

TABLE 2

E.E.C. by 2-methoxyethanol process

| Temp. (°C.) | Ethyl chloroformate charge Mole. equivalents | Addition Time (Min) | Crude Yield (%) | Insoluble O.N.D.C. (%)* | Soluble O.N.D.C. (%) | Erythromycin base (%) |
| --- | --- | --- | --- | --- | --- | --- |
| 23 | 0.9 | 30 | 61 | 13.0 | 0 | 12 |
| 40 | 0.9 | 70 | 76 | 11.1 | 0 | 10 |
| 40 | 0.9 | 60 | 67 | 0 | 4.5 | — |
| 40 | 0.9 | 90 | 76 | 6.4 | 0.1 | 10 |
| 45 | 1.4 | 50 | 94 | 0 | 1.3 | 2 |
| 45 | 1.4 | 50 | 91 | 0 | 1.1 | 3 |
| 55 | 1.4 | 5 | 59[1] | 13.6 | — | — |
| 55 | 1.4 | 60 | 32[1] | 11.7 | — | — |
| 55 | 1.4 | 210 | 65[1] | 3.0 | 0.96 | 44 |
| 50[2] | 1.4 | 270 | 95 | 0 | 1.0 | 5 |
| 50[3] | 1.4 | 225 | 89 | 0 | 1.1 | 4 |
| 50[3] | 1.4 | 240 | 87 | 0 | 2.0 | 5 |

*This material on T.L.C. was found to be a mixture of E.E.C. and erythromycin base and not O.N.D.C. as expected
[1]Pure Yields
[2]Pilot scale run on 4.4 kg base
[3]Pilot scale run on 5.5 kg base

TABLE 3

Variation of 2-methoxyethanol volume

| 2-methoxyethanol volume (ml) | Pure Yield % | Soluble O.N.D.C. % | Insoluble O.N.D.C. % | F. Base % |
| --- | --- | --- | --- | --- |
| 1000 | 65 | 0.96 | 3.0 | <4 |
| 500 | 74 | 0.9 | 5.9 | <4 |
| 250 | 79 | 3.6 | 11.8 | <4 |

Note
[1]E. base input in all cases was 87.3 g
[2]1000 ml represents the normal charge

TABLE 4

Variation of drown-out water volume

| Water Volume (ml) | Pure Yield % | Soluble O.N.D.C. % | Insoluble O.N.D.C. % | E. Base % |
| --- | --- | --- | --- | --- |
| 1000 | 75 | — | 4.0 | <4 |
| 2000 | 78 | 2.2 | 5.0 | <4 |
| 2800* | 65 | 0.96 | 3.0 | <4 |
| 4000 | 80 | — | 3.0 | <4 |
| 8000 | 72 | 3.1 | 6.9 | <4 |

The process described above with reference to the tables is for the first stage of the overall E.E.C. synthesis; we still carry out the refining stage using acetone. It is envisaged that refining could also be carried out from 2-methoxyethanol, with the result that the product would be easier to handle on the plant. This would enable the usual refining step to be eliminated with minor modification to the process—namely the inclusion of a recycling step via an in-line filter.

It is considered there would be little problem in implementing this process modification as the final refining step from acetone could still be included in the overall process, thereby ensuring the nature of the final product is the same as that obtained using our process described herein.

The invention will now be further described with reference to the following Examples.

Examples 7 to 10 and 26, 27 and 36 to 45 are given by way of comparison to show the extent of O.N.D.C. formation and base residue obtained using solvents other than alkanols and alkyl alkanols.

EXAMPLE 1

A solution of 611 g of ethyl chloroformate in isopropanol is added to a solution of 4,400 g of erythromycin in isopropanol containing 4048 g of sodium bicarbonate over a period of 4.3 hours at a temperature of 40°–45° C. Immediately after the addition is completed the inorganic salts are filtered off and the reaction mixture is drowned into a five fold excess of water, aged to complete precipitation and the product is isolated by filtration giving 3,500 g (79% yield). The white crystalline solid is refined by dissolution in acetone and reprecipitated using 100 liters of water.

EXAMPLE 2

A solution of 1132 g of ethyl chloroformate in 2-methoxyethanol is added to a solution of 5.5 kg of erythromycin in 2-methoxyethanol containing 4.2 kg of sodium bicarbonate over a period of 3.75 hours at a temperature of 40°–60° C. After the addition is completed the inorganic salts are filtered off and the reaction mixture is drowned into a threefold excess of water, aged to complete precipitation and the product is isolated by filtration giving 4.9 kg (89%). The white crystalline solid is refined by dissolution in acetone and reprecipitated using water.

EXAMPLE 3

A solution of 18.1 g ethyl chloroformate in 2-methoxyethanol is added to a solution of 87.3 g erythromycin in 2-methoxyethanol containing 67.0 g diisopropylamine, over a period of 3.5 hours at a temperature of 50°–55°. After the addition is complete the inorganic salts are filtered off, the reaction mixture is drowned into three volumes of water, aged to complete precipitation and the product isolated by filtration. The white solid is purified by dissolution in acetone and reprecipitating with water. A yield of 55.6 g (58%) was obtained.

EXAMPLE 4

A solution of 18.1 g ethyl chloroformate in 2-methoxyethanol is added to a solution of 87.3 g erythromycin in 2-methoxyethanol containing 42.0 g sodium carbonate, over a period of 3.5 hours at 50°–55°. On completion of the addition the inorganic salts are filtered off the reaction mixture is drowned into 3 volumes of water, aged to complete precipitation and the product isolated by filtration. After dissolution in acetone and reprecipitation with water, the pure product (63.3 g, 66%) is obtained as a white crystalline solid.

to 5 hours, and carrying out four runs using acetone E.E.C. was prepared and the results shown in Table 5 obtained.

TABLE 5

Experimental data on pilot plant syntheses of erythromycin ethyl carbonate using different solvents

| Solvent | Erythromycin Base (kg) | Temp. (°C.) | Ethyl Chloroformate | Addition Time (Mins) | Product Yield Weight | Product Yield % w/w | O.N.D.C. % Insol | O.N.D.C. % Sol | Base % |
|---|---|---|---|---|---|---|---|---|---|
| 7 Acetone | 2.15 | 20 | 295 g | 15 | 1.4 | 65 | 30.5 | 8.0 | 6 |
| 8 Acetone | 10.0 | 20 | 1.62 kg | 15 | 4.7 | 47 | 28.5 | 5.0 | 6 |
| 9 Acetone | 10.0 | 20 | 1.62 kg | 15 | 6.3 | 63 | 31.9 | 5.2 | 6 |
| 10 Acetone | 9.5 | 20 | 1.54 kg | 30 | 5.0 | 52.6 | 35.0 | 2.0 | 6 |
| 11 Isopropyl alcohol | 7.0 | 40 | 963 g | 75 | 2.2 | 31.4 | 2.0 | 2.7 | 6 |
| 12 Isopropyl alcohol | 4.4 | 35 | 611 | 105 | 2.5 | 57.0 | 2.0 | 4.0 | 5 |
| 13 Isopropyl alcohol | 4.4 | 40 | 611 | 120 | 1.2 | 27.3 | 13 | 11 | 5 |
| 14 Isopropyl alcohol | 4.4 | 45 | 611 | 300 | 2.6 | 59.1 | — | — | — |
| 15 Isopropyl alcohol | 4.4 | 40 | 657 | 315 | 3.0 | 68.2 | 3.0 | 1.0 | 7 |
| 16 Isopropyl alcohol | 4.4 | 40 | 611 | 260 | 3.5 | 79.5 | 3.0 | 6.0 | 4 |
| 17 Isopropyl alcohol | 4.4 | 40 | 611 | 300 | 3.5 | 79.5 | 3.5 | 1.3 | 8 |
| 18 Isopropyl alcohol | 4.4 | 40 | 611 | 300 | 3.1 | 70.5 | 2.9 | 8.5 | 4 |
| 19 Isopropyl alcohol | 4.4 | 40 | 611 | 300 | 3.9 | 88.6 | 11.1* | 4.1 | 4 |
| 20 2-methoxy ethanol | 4.4 | 50 | 906 | 270 | 4.2 | 95 | 0 | 1.0 | 5 |
| 21 2-methoxy ethanol | 5.5 | 50–60 | 1.13 kg | 225 | 4.9 | 89 | 0 | 1.1 | 4 |
| 22 2-methoxy ethanol | 5.5 | 50 | 1.13 kg | 240 | 4.8 | 87 | 0 | 2.0 | 5 |
| 23 2-methoxy ethanol | 5.5 | 40–60 | 1.13 kg | 240 | 5.3 | 96 | 0 | 2.0 | 3 |
| 24 2-methoxy ethanol | 5.2 | 40–60 | 1.13 kg | 200 | 4.9 | 94 | 0 | 2.0 | 2 |
| 25 2-methoxy | 5.5 | 40–60 | 1.13 kg | 210 | 4.6 | 84 | 0 | 2.0 | 3 |

*Mostly inorganic material

EXAMPLE 5

A solution of 2.2 kg ethyl chloroformate in 2-methoxyethanol is added to a solution of 11.0 kg erythromycin in 2-methoxyethanol containing 8.4 kg sodium bicarbonate over a period of 3.5 hours at 50°–55°. After completion of the addition the inorganic salts are filtered off, the reaction mixture is drowned into an equal volume of water, aged to complete precipitation and the product isolated by filtration. The crude product is refined by dissolution in acetone and reprecipitating with water. The yield of white, crystalline product is approximately 75%.

EXAMPLE 6

A solution of 793 g of ethyl chloroformate in alkanol or alkoxyalkanol is added to a solution of 5.5 kg of erythromycin in the same solvent containing 4–5 kg of a suitable base over a period of 3–5 hours at a temperature of 40°–60° C. After the addition is completed the solids are filtered off and the reaction mixture is drowned into an excess of water, aged to complete precipitation and the product is isolated by filtration. The white crystalline solid is refined by dissolution in acetone and reprecipitated using water.

EXAMPLES 7 to 25

Using a procedure similar to that described in Example 6, but varying the addition period from 15 minutes to 5 hours, and carrying out four runs using acetone E.E.C. was prepared and the results shown in Table 5 obtained.

It can be seen from the data in Table 5 that although yields of up to 65% w/w were obtained using acetone, these products contained about 40% of the O.N.D.C. impurity. It is our experience that using acetone the O.N.D.C. impurity content is difficult to control, and also that once present, the soluble O.N.D.C. impurity is impossible to reduce by recrystallization. Refining of crude products made using acetone as solvent with high insoluble O.N.D.C. contents has been found to result in an increase in the soluble O.N.D.C. content.

EXAMPLES 26–45

Synthesis was carried out using a variety of solvents. Except where indicated all reactions were carried out at 55° and the ethyl chloroformate was added over a period of 3.5 hours. The same volume of solvent was used in each case, except for diethyl ether and cyclohexane/acetone (25:1), where the minimum volume needed, to effect dissolution was used.

In the synthesis using cyclohexane and ether, some solid precipitated out of the reaction mixture; the results for both the precipitates and the material remaining in solution are shown in Table 6 below.

TABLE 6

| Solvent | Pure Yield (%) | Insoluble O.N.-D.C. (%) | Soluble O.N.-D.C. (%) | Erythromycin base content (%) |
| --- | --- | --- | --- | --- |
| 26 Acetone | 93 (Crude) | 0 | 4.5 | 10 |
| 27 Methylethyl ketone | 63 | 10 | 6.8 | <4 |
| 28 Methanol | 19 | 0 | 2.5 | 15 |
| 29 Ethanol | 85 | 0 | 4.5 | — |
| 30 Isopropanol | 45 | 0 | 9.8 | — |
| 31 N-propanol | 32 | 0 | 6.4 | <4 |
| 32 Ethylene glycol | 5 | 0 | 3.7 | 4.0 |
| 33 Glycerol | 9 | 0 | 8.7 | 4.0 |
| 34 Propan-1,2-diol | 23 | 0 | 9.3 | 4.0 |
| 35 2-methoxy ethanol | 65 | 3.0 | 1.0 | <4.0 |
| 36 Tetrahydrofuran | 40 | 9.3 | 10.5 | <4.0 |
| 37 Methyl formate | 0 | — | — | — |
| 38 Ethyl formate | 0 | — | — | — |
| 39 Methyl acetate | 42 (Crude) | — | — | — |
| 40 Acetonitrile | 79 | 12.0 | 6.8 | <4 |
| 41 Dimethylsulphoxide | 32 | 10.5 | 10.5 | >>4 |
| 42 Diethyl-ether | 47 (Crude) | 26.7 | 6.1 | — |
| 43 Diethyl-ether[1] | 53 (Crude) | 76.7 | 4.4 | — |
| 44 Cyclohexane/acetone | 48 (Crude) | 62.0 | 0.1 | — |
| 45 Cyclohexane/acetone[2] | 50 (Crude) | 40.5 | 27.5 | — |

[1] Material precipitated from reaction mixture
[2] Material precipitated from reaction mixture It can be seen from the above results in Table 6 that the use of solvents outside the scope of those used in accordance with the invention has caused extensive O.N.D.C. formation (approximately 50% in the cases of cyclohexane/acetone, and diethyl ether) or poor or zero yield. In the case of high O.N.D.C. formation it may be that in these solvents E.E.C. reacts at a more rapid rate with ethyl chloroformate than does erythromycin base, so that as soon as any E.E.C. is formed it is converted into O.N.D.C. It would appear in the case of cyclohexane/acetone and diethyl ether that as the yield is of the order of 50–60%, the ethyl chloroformate which is added in a 1.1:1 ration of erythromycin base, is being used for the second stage of the reaction to form O.N.D.C. leaving approximately 50% of the initial base unreacted.

In the case of methanol we found that 90% hydrolysis of E.E.C. to base occurs in 50% methanol/water after 3 hours at 60° C. For this reason methanol is currently considered the least preferred solvent for use in accordance with the invention.

The base content of the product from most runs was generally ≦4% by weight. It runs not in accordance with the invention the presence of insoluble O.N.D.C. was noticeable; it runs in accordance with the invention, however, by contrast, there was in most cases a complete absence of insoluble O.N.D.C.

The O.N.D.C. impurity is the O,N-dicarbethoxy derivative of erythromycin, resulting from further reaction of the erythromycin ethyl carbonate product with ethyl chloroformate. This impurity was previously referred to in the B.P.C. 1968 as "diester". This impurity appear to exist in two crystalline forms (one soluble in diethyl ether and the other insoluble), both of which are formed using the acetone process.

We claim:

1. In a process for preparing erythromycin ethyl carbonate by reacting ethyl chloroformate with erythromycin in the presence of a weak base and thereafter separating erythromycin ethyl carbonate from the reaction mixture, the improvement comprising conducting the reaction in a $C_2$–$C_5$ alkanol or a 2-methoxyethanol solvent.

2. A process according to claim 1, wherein the alkanol is isopropyl alcohol.

3. A process according to claim 1 wherein the weak base is sodium bicarbonate.

4. A process according to claim 1 wherein the reaction temperature is 35°–85° C.

5. A process according to claim 4, wherein the reaction temperature is 50°–55° C.

6. A process according to claim 1, wherein the reaction period is 3 to 5 hours.

7. A process according to claim 1, wherein after reaction any insoluble salt is removed, the filtrate drowned with at least an equal volume of water, and the aqueous mixture aged to precipitate the erythromycin ethyl carbonate.

* * * * *